United States Patent [19]

Wang et al.

[11] Patent Number: 5,105,035

[45] Date of Patent: Apr. 14, 1992

[54] PROCESS FOR REMOVING VINYLIDENE CHLORIDE AND OTHER UNSATURATED COMPOUNDS FROM 1,1-DICHLORO-1-FLUOROETHANE BY HYDROGENATION

[75] Inventors: Li Wang, Bloomingdale; Stephen F. Yates, Arlington Heights; Russell W. Johnson, Elmhurst, all of Ill.

[73] Assignee: Allied-Signal Inc., Morris Township, Morris County, N.J.

[21] Appl. No.: 706,836

[22] Filed: May 29, 1991

[51] Int. Cl.$^5$ .............................................. C07C 27/26
[52] U.S. Cl. .................................... 570/178; 570/177
[58] Field of Search ............... 570/177, 178, 167, 175, 570/176, 101

[56] References Cited

U.S. PATENT DOCUMENTS

| | | | |
|---|---|---|---|
| 2,697,124 | 12/1954 | Mantell | 260/653 |
| 2,802,887 | 8/1957 | Miller et al. | 260/653 |
| 2,894,044 | 7/1959 | Prill | 260/653.7 |
| 3,564,064 | 2/1971 | Nakagawa | 260/653.5 |
| 3,833,676 | 10/1974 | Ukaji et al. | 260/653.7 |
| 4,145,367 | 3/1979 | Boozalis et al. | 570/262 |
| 4,319,060 | 3/1982 | Cunningham et al. | 570/177 |
| 4,940,824 | 7/1990 | Yates | 570/179 |
| 4,940,825 | 7/1990 | Yates | 570/179 |
| 4,950,816 | 8/1990 | Tung et al. | 570/179 |

FOREIGN PATENT DOCUMENTS

WO90/08750 1/1990 PCT Int'l Appl. .

Primary Examiner—Howard T. Mars
Assistant Examiner—Kimberly J. Kestler
Attorney, Agent, or Firm—Harold N. Wells; Gerhard H. Fuchs; Jay P. Friedenson

[57] ABSTRACT

Vinylidene chloride and other unsaturated impurities are removed from HCFC-141b by reaction with hydrogen over a catalyst such as palladium on alumina.

16 Claims, No Drawings

PROCESS FOR REMOVING VINYLIDENE CHLORIDE AND OTHER UNSATURATED COMPOUNDS FROM 1,1-DICHLORO-1-FLUOROETHANE BY HYDROGENATION

BACKGROUND OF THE INVENTION

This invention relates to the purification of 1,1-dichloro-1-fluoroethane, also designated HCFC-141b, which has been of particular interest as a replacement for chlorofluorocarbons having similar physical properties, particularly HCFC-11 and HCFC-113. HCFC-141b may be prepared by reaction of vinylidene chloride or trichloroethane with HF. Such processes are disclosed, for example, in U.S. Pat. Nos. 2,894,044 and 3,833,676.

Many by-products are formed, containing varying numbers of hydrogen, chlorine, and fluorine atoms on methane, ethane, and ethylene molecules. Some compounds are relatively harmless since their presence does not greatly alter the physical properties for which HCFC-141b is useful but others must be removed from the product. These by-products and the unreacted feed material may be separated by distillation where possible. Since vinylidene chloride is toxic, it must be removed from HCFC-141b. Vinylidene chloride has a boiling point close to that of HCFC-141b making it difficult to separate them by distillation. After distillation of the crude product, vinylidene chloride will still be present in amounts up to about 2000 ppm (wt.). If not separated, vinylidene chloride might be present in much larger amounts, say up to several percent or more of the HCFC-141b. It should be reduced to below 500 ppm according to the specifications of the Panel for Advancement of Fluorocarbon Test (PAFTII). Preferably, the vinylidene chloride should be below about 200 wt. ppm.

Dichloroacetylene is another toxic impurity. It may be present in crude HCFC-141b in amounts up to about 25 ppm (wt.) or more and should be removed to below 1 ppm to meet the specifications referred to above.

Various methods have been suggested for removing vinylidene chloride and dichloroacetylene from waste streams. For example, in U.S. Pat. No. 4,940,824 it is shown that vinylidene chloride can be removed from HCFC-141b using carbon molecular sieves and in U.S. Pat. No. 4,940,825 that dichloroacetylene also can be removed by carbon molecular sieves from HCFC-141b or from vinylidene chloride.

In U.S. Pat. No. 4,948,479 Brooks et al. disclose the use of photochlorination in the liquid phase to add chlorine to unsaturated carbon compounds, including vinylidene chloride, which can be more readily separated from HCFC-141b.

In co-pending U.S. patent application Ser. No. 07/627,070, photochlorination in the vapor phase is shown to have advantages over the liquid phase process.

Hydrogenation of chlorofluorocarbons to remove chlorine atoms has been suggested in the art. Mantell, in U.S. Pat. No. 2,697,124 disclosed the use of hydrogen and a catalyst to dehalogenate saturated fluorohalocarbons and to produce an unsaturated product. Other examples of related processes include U.S. Pat. No. 2,802,887 in which a Pd on carbon catalyst is shown to be useful for hydrogenating the olefin 1-chloro 1,2,2-trifluoroethylene to the corresponding olefin 1,2,2-trifluoroethylene. Similarly, in U.S. Pat. No. 3,564,064 Pt or Pd on carbon or alumina are shown to be useful for the same hydrogenation reaction. Such processes were not intended to remove small amounts of impurities from a halocarbon product and the reaction products are unsaturated, that is, the double bond is not hydrogenated. Thus, such processes are contrary to the objectives of the present invention as will be seen.

In WO 90/08750 saturated halocarbons are hydrogenated to remove olefin impurities. However, only fluorocarbons and fluorohydrocarbons are included as feedstocks, that is, compounds containing chlorine atoms such as the compound of interest to the present inventors, namely HCFC-141b (1-fluoro 1,1-dichloroethane) would not be included. In view of the art suggesting that chlorine atoms can be readily displaced by hydrogen it may have been believed by the inventors in the '750 application that compounds containing chlorine atoms could not be effectively purified by hydrogenation without significant loss of such compounds.

We have now found that vinylidene chloride can be removed by hydrogenation to products which can be separated easily from HCFC-141b by distillation or other means as desired.

SUMMARY OF THE INVENTION

Vinylidene chloride is removed from a mixture consisting substantially of 1,1-dichloro-1-fluoroethane (HCFC-141b), typically containing up to about 2000 wt. ppm vinylidene chloride, by contacting with hydrogen in the presence of a suitable hydrogenation catalyst, preferably palladium on an alumina or carbon support. The vinylidene chloride can be reduced to a predetermined value, preferably below 200 wt. ppm, even to below 1 wt. ppm by hydrogenation and hydrodechlorination, as it is converted to 1,1-dichloroethane, chloroethane, or ethane, which have boiling points differing from that of HCFC-141b and can be easily separated by distillation. Other unsaturated compounds such as dichloroacetylene are also removed by hydrogenation to other more-easily separated derivatives.

The reaction can be carried out in either the liquid or gas phases, the gas phase being preferred. The temperature is maintained at a relatively low temperature, below about 100° C., preferably 15° to 40° C., to selectively react hydrogen with vinylidene chloride while having minimal effect upon the HCFC-141b.

DETAILED DESCRIPTION OF THE INVENTION

While the HCFC-141b produced by reacting vinylidene chloride or trichloroethane with HF over a catalyst will contain a variety of byproducts such as $C_4H_5F_5$(R-365), $CF_2ClCH_3$(R-142b), $CCl_2=CH_2$(R-1130a), $CCl_3CH_3$(R-140a), $CFCl=CH_2$(HFC-1131a), it is of particular importance to remove vinylidene chloride and dichloroacetylene from the crude product. Preliminary separation of HCFC-141b by distillation will leave up to about 2000 wt. ppm of vinylidene chloride and up to about 25 wt. ppm of dichloroacetylene. If not separated, the vinylidene chloride content of HCFC-141b could be much higher, up to several percent or more. It should be noted here that the vinylidene chloride content is not a critical factor in defining the present invention. In the process of the invention, these and other unsaturated compounds are hydrogenated and hydrodechlorinated. The products of hydrogenation and hydrodechlorination have boiling points which differ from that of HCFC-141b and can be readily separated. At the same time the loss by dechlorination of the major constituent, HCFC-141b, to HCFC-151a is minimal.

The hydrogenation of vinylidene chloride, dichloroacetylene, and any other unsaturated compounds present in impure HCFC-141b may be characterized as a "selective" hydrogenation. That is, the objective is to convert only the unsaturated compounds and to avoid displacing the chlorine atoms from HCFC-141b. The process conditions have been found which avoid excessive hydrogenation and hydrodechlorination and efficiently convert vinylidene chloride to easily separable products. The principal product is ethane and the amounts of 1,1-dichloroethane ($CH_2ClCH_2Cl$ or 150a) and chloroethane ($CH_3CH_2Cl$ or 160) formed are small. Other unsaturated compounds susceptible to this hydrogenation, such as dichloroacetylene, may also be converted to their saturated equivalents.

Process Conditions

In our process, crude HCFC-141b, which typically contains up to about 2000 wt. ppm of vinylidene chloride (but could be higher) and up to about 25 wt. ppm or more of dichloroacetylene, along with minor amounts of other byproducts such as those mentioned above will be contacted in the liquid or vapor phase with hydrogen in the presence of a suitable catalyst, preferably palladium on an alumina or carbon support.

When operating with the HCFC-141b mixture in the vapor phase, a low pressure is employed which will assure that the HCFC-141b is vaporized at the reaction temperature with the amount of hydrogen present. Generally, pressures in the range of about 100 to 600 kPa are suggested. Operation at room temperature and atmospheric pressure is possible and employing such conditions would be desirable. The amount of hydrogen relative to the amount of HCFC-141b may be varied from a mol ratio of about 0.1/1 to about 10/1, preferably from about 0.5/1 to about 2/1. The temperature will be selected to optimize the hydrogenation and hydrodechlorination of vinylidene chloride and other unsaturated impurities and to minimize the effect on HCFC-141b. Temperatures in the range of 0° to 100° C. are possible, but the range of 15° to 40° C. is preferred.

When operating with a liquid phase mixture, it is a feature of the invention that no more than the amount of hydrogen which will dissolve in the HCFC-141b stream need be used. Less hydrogen may be used than the amount which will saturate the liquid HCFC-141b. This means that the process operates with only a liquid phase present and separation and recirculation of excess hydrogen is unnecessary. Any residual hydrogen will be separated in the distillation process which removes the impurities from HCFC-141b and then disposed of, i.e., by burning or other convenient means. Excess hydrogen above that needed could be used to create a two-phase process, but would not be preferred. Typically, the amount of hydrogen dissolved in liquid HCFC-141b would be about 0.003 to 0.02 mols of $H_2$ for each mol of HCFC-141b.

Hydrogen and impure HCFC-141b are contacted in pressurized saturator or other suitable means familiar to one skilled in the art. The pressure in the contactor may be varied to adjust the amount of hydrogen which dissolves in the HCFC-141b. Typically, a pressure of about 400 to 4000 kPa would be expected to be suitable, preferably about 800 to 2000 kPa. The liquid HCFC-141b, now saturated or under-saturated with hydrogen is passed over a bed of a suitable hydrogenation catalyst, such as those to be discussed below. The catalyst typically will be in the form of a packed bed of particles of about 0.1 to 5 mm in size, although other means of contacting a solid catalyst with a liquid could be employed, such as fluidized beds or a slurry reactor.

The hydrogenation of vinylidene chloride and dichloroacetylene requires a liquid hourly space velocity of about 0.5 to 20 $hr^1$ for HCFC-141b containing about 2000 wt.ppm of vinylidene chloride.

The temperature employed may vary but may be from about 0° C. to 100° C., preferably about 15° to 40° C.

The pressure selected will be a convenient value to suit the processing conditions for HCFC-141b and will maintain HCFC-141b in the liquid phase at the selected temperature.

After the HCFC-141b has been hydrogenated, the dichloroethane, chloroethane, and ethane produced from vinylidene chloride may be separated from the HCFC-141b, as, for example, by distillation, since the boiling points are no longer close to that of HCFC-141b.

Catalysts

Effective hydrogenation catalysts include members of the group consisting of Pd on alumina, Pd on carbon, Pd on aluminum fluoride, Ni on alumina, Co on alumina, Pt on alumina, Pt on carbon, Pt on aluminum fluoride, unsupported Ni, Co, Pd, or Pt, and combinations of Pd, Pt, Ni, and Co either supported or unsupported. Preferably Pd is used, supported either on alumina or carbon of the types familiar to those skilled in the art.

The amount of the active metal used will depend upon the metal selected and whether it is supported or not. For unsupported metals, such as the base metals Ni and Co, these would be in the form of powder, gauze, or sponge such as Raney nickel and the liquid hourly space velocity would be in the range of 0.5 to 5 $hr^{-1}$. For supported metals, the concentration would be in the range of 1 to 30 wt. % based on the entire catalyst, particularly 5 to 15 wt. % for the base metals and 0.1 to 10 wt. % for the noble metals, such as the preferred palladium.

As mentioned above, supported catalysts may be prepared by various techniques familiar to those skilled in the art, such as impregnation of the supports with solutions of the metal compounds, e.g., nitrates, chlorides, acetates, and the like or metal complexes such as $Pd(NH_3)_4Cl_2$, $Pt(NH_3)_4Cl_2$ and the like. The supports may be aluminas, activated carbon, aluminum fluoride or others familiar to skilled workers. In particular, Pd on an alumina or carbon support has been found effective for the hydrogenation process of the invention.

EXAMPLE 1

A catalyst containing 2 wt.% Pd on gamma alumina was prepared by impregnating the alumina with an aqueous $H_2PdCl_4$ solution. Ninety-eight grams (98) of γ-alumina was contacted with an aqueous solution of $H_2PdCl_4$ prepared by mixing 40 g of 5 wt.% $H_2PdCl_4$ solution with 2.8 g of 37 wt % HCl, 4.3 g of 70 wt. % $HNO_3$ and 144 g of deionized water. After contacting for 30 minutes at room temperature, the mixture was heated to 80° C. to evaporate the residual solution. The dried solids were thereafter calcined in a muffle furnace at 350° C. for 2 hrs.

EXAMPLE 2

A catalyst prepared as in Example 1 was ground to 40–80 mesh size and a 2 mL sample was taken and placed in a 6.35 mm i.d. reactor. The catalyst was reduced with $H_2$ at 350° C. for 2 hrs prior to introducing the feed HCFC-141b containing 1000 wt.ppm vinylidene chloride was fed into the reactor at a rate of 20 mL/hr and hydrogen was supplied at 80 mL/min which provided a $H_2$/141b mol ratio of 1/1. The reaction was carried out at room temperature for about 8 hours.

EXAMPLE 3

Another 2 mL sample of 40–80 mesh size catalyst prepared as in Example 1 was placed in the 6.35 i.d. reactor. The catalyst was reduced with $H_2$ as in Example 2. HCFC-141b containing 1000 wt.ppm Vinylidene chloride 1130a) was saturated with $H_2$ at 1379 kPa (gauge) (200 psig) and then passed over the catalyst at that pressure and at room temperature for 8 hours.

The reactor effluents from Example 2 and 3 were passed through a dry ice-acetone trap (−78° C.) to collect the products. The liquid was analyzed with Hewlett-Packard 5890 GC and GC-MSD equipment. The results of the two examples are presented in the following table. The components are generally designated by their number from the ASRE nomenclature.

TABLE A

| | | Effluent | |
|---|---|---|---|
| Component[1] | Feed[2] | Example 2[2] (Gas Phase) | Example 3[2] (Liquid Phase) |
| 142b | 7.92 | 6.33 | 7.53 |
| 365 isomers | 0.12 | 0.11 | 0.12 |
| 141b | major | major | major |
| 1130a | 1.37 | 0 | 0 |
| 364 isomers | 0.12 | 0.12 | 0.13 |
| 1130 | 0.04 | 0 | 0 |
| 140a[3] | 9.88 | 9.88 | 9.88 |
| 362 isomers | 1.00 | 0.51 | 0.98 |
| 361 isomers | 2.83 | 0.21 | 2.87 |
| unknown | — | 0.03 | 0 |
| 160 | — | 0.03 | 0 |
| unknown | — | 0.08 | 0.04 |
| 150a | — | 0.05 | 0.12 |
| | | (42 ppm) | (107 ppm) |
| 381 isomers | — | 0.40 | 0 |

[1] Components as designed by ASRE
142b = $CClF_2CH_3$
365 = $C_4H_5F_5$
141b = $CCl_2FCH_3$
1130a = $CH_2=CCl_2$
364 = $C_4H_5F_4$
1130 = $CHCl=CHCl$
140a = $CH_3CCl_3$
362 = $C_4H_5F_2$
361 = $C_4H_5F_1$
160 = $CH_3CH_2Cl$
[2] amounts of each component given in area %
[3] 140a assumed unconverted and values for each component normalized to conform with assumption It will be seen that 1130 and 1130a (vinylidene chloride) are completely removed. No measureable amounts of the hydrogenated analogs of HCFC-141b were detected (i.e., 151 and 161).

We claim:

1. A process for removing vinylidene chloride and other unsaturated compounds from 1,1-dichloro-1-fluoroethane (HCFC-141b) comprising
   contacting a mixture consisting essentially of HCFC-141b and a minor amount of vinylidene chloride with hydrogen in the presence of a hydrogenation catalyst at a temperature below about 100° C., thereby reducing the concentration of vinylidene chloride to below 500 pm by hydrogenation and hydrodechlorination of vinylidene chloride.

2. The process of claim 1 wherein said hydrogenation catalyst is at least one member selected from the group consisting of Pd on alumina, Pd on carbon, Pd on aluminum fluoride, and unsupported Ni, Co, Pd, or Pt.

3. The process of claim 2 wherein said hydrogenation catalyst is Pd on an alumina support.

4. The process of claim 1 wherein the contacting of (a) is carried out at a temperature of about 15° to 40° C.

5. The process of claim 1 wherein the vinylidene chloride content of HCFC-141b initially is up to about 2000 wt. ppm.

6. The process of claim 1 wherein the vinylidene chloride content of HCFC-141b after the contacting of (a) is less than 200 wt. ppm.

7. The process of claim 1 wherein the concentration of vinylidene chloride is reduced to below 1 wt. ppm.

8. The process of claim 1 wherein said mixture of (a) is contacted with hydrogen in the vapor phase.

9. The process of claim 8 wherein the mol ratio of hydrogen to HCFC-141b is about 0.1/1 to 10/1.

10. The process of claim 1 wherein said mixture of (a) is contacted with hydrogen in the liquid phase.

11. The process of claim 10 wherein the HCFC-141b is saturated with hydrogen.

12. The process of claim 10 wherein the HCFC-141b is under-saturated with hydrogen.

13. The process of claim 9 wherein the mol ratio of hydrogen to HCFC-141b is about 0.003/1 to 0.02/1.

14. The process of claim 1 wherein the HCFC-141b contains dichloroacetylene.

15. The process of claim 1 wherein said contacting employs a liquid hourly space velocity of about 0.5 to 20 $hr^{-1}$ based on HCFC-141b.

16. The process of claim 1 further comprising the step of separating HCFC-141b from the products of hydrogenation and hydrodechlorination by distillation.

* * * * *